(12) United States Patent
Hwang et al.

(10) Patent No.: US 9,526,925 B2
(45) Date of Patent: Dec. 27, 2016

(54) VISCOUS ALCOHOL-CONTAINING SUNSCREEN COMPOSITIONS

(75) Inventors: Hui-Ing Donna Hwang, Leonia, NJ (US); Grace Riccardi, Jersey City, NJ (US); Christine M. Popoff, Morganville, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 85 days.

(21) Appl. No.: 13/474,162

(22) Filed: May 17, 2012

(65) Prior Publication Data

US 2013/0309182 A1    Nov. 21, 2013

(51) Int. Cl.
| | | |
|---|---|---|
| *A61K 8/00* | (2006.01) |
| *A61Q 17/04* | (2006.01) |
| *A61K 8/73* | (2006.01) |
| *A61K 8/81* | (2006.01) |
| *A61K 8/04* | (2006.01) |

(52) U.S. Cl.
CPC .............. *A61Q 17/04* (2013.01); *A61K 8/042* (2013.01); *A61K 8/73* (2013.01); *A61K 8/731* (2013.01); *A61K 8/8182* (2013.01); *A61K 2800/48* (2013.01)

(58) Field of Classification Search
CPC ........ A61K 8/922; A61K 31/405; A61K 8/04; A61K 8/31; A61K 8/345; A61K 8/37; A61K 8/375; A61K 8/416; A61K 8/55; A61K 8/731; A61K 8/732; A61Q 19/00; A61Q 15/00; A61Q 17/02; A61Q 17/04; A61Q 1/14; A61Q 5/02; A61Q 5/12; A61Q 9/02
See application file for complete search history.

(56) References Cited

U.S. PATENT DOCUMENTS

| | | | |
|---|---|---|---|
| 4,440,778 A | * | 4/1984 | Matsui et al. ................. 514/420 |
| 2003/0152540 A1 | * | 8/2003 | Putman et al. .............. 424/70.1 |
| 2005/0079141 A1 | * | 4/2005 | Zander et al. .................. 424/59 |
| 2006/0251606 A1 | * | 11/2006 | Coffindaffer et al. ..... 424/70.31 |
| 2009/0269376 A1 | * | 10/2009 | Lundberg et al. ............. 424/401 |

OTHER PUBLICATIONS

International Search Report and Written Opinion Dated Apr. 29, 2013 From PCT Application No. PCT/US2013/35100.

* cited by examiner

*Primary Examiner* — Nannette Holloman
(74) *Attorney, Agent, or Firm* — Edgewell Personal Care Brands, LLC

(57) ABSTRACT

The present disclosure provides a composition that maintains a high and desirable viscosity while having a high amount of alcohol. Suitable thickeners and gelling agents are mixed with the alcohol to achieve this effect. An emulsion stabilizer can also be added. These components can also be combined with a sunscreen. The resulting composition provides benefits such as cooling and desirable skin feel, but is still easily spreadable and viscous enough to function effectively as a sunscreen.

19 Claims, No Drawings

VISCOUS ALCOHOL-CONTAINING SUNSCREEN COMPOSITIONS

BACKGROUND OF THE DISCLOSURE

1. Field of the Disclosure

The present disclosure relates to sunscreen compositions. More particularly, the present disclosure relates to sunscreen compositions having a relatively high amount of alcohol while still retaining one or more favorable viscosity properties.

2. Description of the Related Art

In the field of sunscreen compositions, a rheology modifier or thickener can be used to achieve a desired viscosity. Alcohols, however, particularly ethyl alcohol, can interfere with the viscosity-boosting mechanisms employed by most rheology modifiers. In sunscreen compositions, it can thus be very difficult to use an alcohol, since the composition will be thin, and not provide adequate coverage or UVA/UVB protection to a user.

The present disclosure provides a composition that addresses these deficiencies.

SUMMARY OF THE DISCLOSURE

There is provided in one embodiment of the present disclosure a composition that comprises: 0.1 to 10 percent, based on the weight of the total composition, of a rheology modifying agent selected from the group consisting of a copolymer of acryloyldimethyltaurine and vinylpyrrolidone, a copolymer of acrylic acid and vinylpyrrolidone, acrylic-based anionic polymers, carbomers, and any combinations thereof; 0.01 to 5 percent, based on the total weight of the composition, of a gelling agent selected from the group consisting of starch, modified starch, cellulose, cellulose gum, pectin, gelatin, agar, alginate, gellan gum, and any combinations thereof; and 5 to 40 percent, based on the total weight of the composition, of an alcohol.

There is also provided such a composition that further comprises 0.01 to 5 percent, based on the total weight of the composition, of an emulsion stabilizer comprising natural fibers.

There is further provided in another embodiment of the present disclosure a second composition that comprises: 0.1 to 10 percent, based on the weight of the total composition, of a rheology modifying agent selected from the group consisting of a copolymer of acryloyldimethyltaurine and vinylpyrrolidone, a copolymer of acrylic acid and vinylpyrrolidone, acrylic-based anionic polymers, carbomers, and any combinations thereof; 0.01 to 5 percent, based on the total weight of the composition, of a gelling agent selected from the group consisting of polysaccharides, polysaccharide gums, and a combination thereof; and 20 to 30 percent, based on the total weight of the composition, of an alcohol selected from the group consisting of aliphatic alcohols having one to four carbons.

There is still further provided for such second composition that it may further comprise 0.01 to 5 percent, based on the total weight of the composition, of an emulsion stabilizer comprising natural fruit fibers.

DETAILED DESCRIPTION OF THE DISCLOSURE

The present disclosure provides a composition containing high amounts of alcohol previously not thought attainable for the above-described reasons (i.e., the adverse effects on viscosity). The compositions of the present disclosure provide protection from both UVA and UVB radiation, but also possess a cooling ability, and desirable feelings to the touch for the user. These latter benefits are provided by the alcohol. The compositions of the present disclosure have alcohol concentrations or amounts in the relatively high ranges discussed below, yet still form a gel-like or viscous structure. Accordingly, the compositions of the present disclosure provide the benefits associated with alcohol, such as cooling, and desirable sensory characteristics, without any of the associated disadvantages. The compositions of the present disclosure also satisfy the broad UVA/UVB spectrum requirements listed in the 2011 Food and Drug Administration's final rules.

"Gel-like" is defined in the present disclosure as referring to a substance or composition having a texture between that of a cream and a rigid, solid structure. Creams are typically either semi-solid oil-in-water or water-in-oil emulsions. The compositions of the present disclosure are also water-in-oil emulsions or oil-in-water emulsions, preferably the former, but they are more elastic than typical creams. They are not so rigid, however, that they break up upon application to the skin, as solids would. The compositions of the present disclosure are easily spreadable upon application.

The compositions of the present disclosure comprise an alcohol compatible rheology modifying agent. The rheology modifying agent may be a copolymer obtained by copolymerization of acryloyldimethyltaurine and vinylpyrrolidone, a copolymer obtained by copolymerization of acrylic acid and vinylpyrrolidone, acrylic-based anionic polymers, carbomers, and any combination thereof. The rheology modifying agent is present in an amount of 0.1 to 10 weight percent, based on the weight of the total composition.

The compositions of the present disclosure also have a gelling agent that forms a fluid elastic gel-like texture. The gelling agent can be a starch, modified starch, cellulose, cellulose gum, pectin, gelatin, agar, alginate, gellan gum, or any combinations thereof. in one embodiment, the gelling agent is a polysaccharide, polysaccharide gum, or a combination thereof. The gelling agent is present in an amount of 0.01 to 5 weight percent, based on the total weight of the composition. Typically, these gelling agents are used in fragrance or food applications, not in cosmetic products such as sunscreens. The present disclosure has discovered that the gelling agent works particularly well with any of the above-described rheology modifiers to stabilize the compositions of the present disclosure.

The compositions of the present disclosure also have an emulsion stabilizer. The emulsion stabilizer can comprise natural fibers, such as those from leaves, flowers, wood, or fruits. In one embodiment, the emulsion stabilizer is made from fruit pulp. An example of an emulsion stabilizer including fruit pulp is citrus surantium sinensis (orange) fiber, sold under the tradename Imulsi-Fi™ A30. The Imulsi-Fi™ A30 stabilizer has natural fibers, including tightly bound soluble and insoluble fibers, together in a matrix with proteins and sugars. It also has a distinctive cellular structure and a unique chemical composition that enables both hydrophilic and lipophilic properties to stabilize the emulsion. The emulsion stabilizer helps to prevent the composition from becoming too hard or solid, which would break up upon application to the user's skin. The emulsion stabilizer, particularly the above-described fibers, helps to keep the composition gel-like. The emulsion stabilizer is present in an amount of 0.01 to 5 weight percent, based on the total weight of the composition.

The compositions of the present disclosure also have one or more alcohols. In one embodiment, the alcohols are volatile aliphatic alcohols having from 1 to 4 carbon atoms, or any mixtures of alcohols having from 1 to 4 carbon atoms. The term "volatile" refers to a liquid that quickly evaporate after contact with the user's skin. Ethanol is an example of a volatile alcohol. The alcohols are present in an amount of 5 to 40 weight percent, 10 to 40 weight percent, or 20 to 30 weight percent, based on the total weight of the composition. Above the stated ranges, the observed sensory benefits provided by the alcohol (e.g., cooling sensation) start to drop off or plateau. Below the stated weight ranges, the benefits are not observed.

In the above stated weight ranges for each component, each range includes all subranges therebetween. For example, 10 to 40 weight percent includes that range and all subranges between 10 and 40 weight percent.

As previously discussed, the one or more rheology modifiers or thickeners can be used to achieve a desired viscosity in a composition. Common rheology modifiers come from both natural and synthetic sources. Examples of natural rheology modifiers are starch, cellulose, alginate, agar, carageenan, gelatin, guar gum, pectin and xanthan gum. Examples of synthetic rheology modifier are fumed silica, sodium carboxymethylcellulose (CMC), acrylic-based anionic polymers, carbomer, hydrophobically modified acrylic-based polymers, hydrophobic ally modified hydroxyethylcellulose, hydroxyethylcellulose, and hydrophobic modified ethoxylated urethane resins (the rheology modifiers suitable in the present disclosure are those described above).

There are several common thickening mechanisms employed by rheology modifiers. These include: creating polymer entanglements when dispersed in water; creating hydrogen-bonding between thickeners and water; creating ionic repulsion by neutralizing anionic polymers with common bases such as sodium hydroxide (NaOH) or triethanolamine (TEA); creating hydrophobic association; and the combination of any of the above.

The addition of alcohol, particularly ethyl alcohol, to an emulsion can interfere with all thickening mechanisms mentioned above and, as a result, reduce emulsion viscosity. Without being bound by any theory, it is believed that the alcohol interferes with at least the hydrogen-bonding thickened mechanism discussed above. Table I below is an example of the impact of 30% ethyl alcohol on composition viscosity. The results show that the viscosity of the emulsion containing ethyl alcohol (Sample 2) is reduced by approximately 37% from the control (Sample 1), which contains no alcohol.

TABLE I

The Impact of 30% Ethyl Alcohol on Emulsion Viscosity

| INCI NAME | FUNCTION/ DESCRIPTION | wt. % Sample 1 | wt. % Sample 2 |
|---|---|---|---|
| DI Water | Solvent | 75.43 | 45.43 |
| Disodium EDTA | Chelating Agent | 0.05 | 0.05 |
| Sodium Acryloyldimethyltaurate/VP Crosspolymer | Thickener | 0.85 | 0.85 |
| Glycerin | Humectant | 3.00 | 3.00 |
| Ethylhexyl Palmitate | Solvent | 5.00 | 5.00 |
| Dimethicone | Skin Conditioning Agent | 1.00 | 1.00 |
| Octocrylene | Sunscreen Active | 4.00 | 4.00 |
| Oxybenzone | Sunscreen Active | 3.00 | 3.00 |

TABLE I-continued

The Impact of 30% Ethyl Alcohol on Emulsion Viscosity

| INCI NAME | FUNCTION/ DESCRIPTION | wt. % Sample 1 | wt. % Sample 2 |
|---|---|---|---|
| Avobenzone | Sunscreen Active | 2.50 | 2.50 |
| Cetearyl Alcohol | Emulsifier | 2.50 | 2.50 |
| Dicetyl Phosphate Ceteth-10 Phosphate Methylparaben, Propylparaben, Phenoxyethanol | Preservative | 1.10 | 1.10 |
| Triethanolamine | pH Adjuster | 0.23 | 0.23 |
| Acrylates/C12-22 Alkyl Methacrylate Copolymer | Film Former | 1.00 | 1.00 |
| Sodium Ascorbl phosphate and Tocopheryl Acetate | Antioxidant | 0.02 | 0.02 |
| *Aloe Barbadensis* Leaf Juice, Panthenol, and water | Skin Conditioning Agent | 0.02 | 0.02 |
| Fragrance | Fragrance | 0.30 | 0.30 |
| Ethanol | Solvent | 0.00 | 30.00 |
| VISCOSITY in centipoise @ shear rate = 1 | | 79670 | 50400 |

The viscous alcohol-containing sunscreen composition of the present disclosure enables the formation of an elastic fluid gel-like structure, to entrap the volatile alcohol within its network, to quickly release volatile alcohol under stress, and to provide instant cooling during the application. This viscous alcohol-containing sunscreen composition is a shear-thinning emulsion, meaning that it thins as stress is applied, and is capable of providing good sensory properties. When applied on skin, it spreads easily and leaves skin with non-tacking feel.

The composition of the present disclosure can be measured by a rheometer (model: Anton Paar MCR301). Combining the sensory information and the rheology profile, the present disclosure has determined that the following parameters can be used to determine ideal ranges for viscosity or rheological characteristics of the composition: (1) a ratio of the loss (or viscous; G") modulus to the storage (or elastic; G') modulus lower than 0.19, preferably, lower than 0.18; (2) a flow point range from 20 Pa to 200 Pa, preferably, from 30 Pa to 100 Pa; and (3) at shear rate=1, a viscosity of 10,000 to 90,000 centipoise, preferably, 40,000 to 60,000 centipoise. These desirable properties can be achieved in the compositions of the present disclosure by balancing the rheology modifying agent, gelling agent, and emulsion stabilizer. When the term "high viscosity" is used in the present disclosure, it refers to a composition having one or more of the three characteristics described immediately above.

In Table II below, base formula A according to the present disclosure is shown. Table III shows base formula A with several different rheology modifiers. Rheology measurements in conjunction with sensory measurements are conducted to determine favorable thickeners for this invention discussed above. As shown in Table III, Sample 5 and Sample 6 are within the optimum range mentioned in the disclosure and have the advantages in rub-in and more cooling sensation, when compared to other Samples listed in Table III.

TABLE II

Base Formula A

| INCI NAME | FUNCTION/DESCRIPTION | wt. % Base Formula |
|---|---|---|
| DI Water | Solvent | QS. To 100 |
| Ethanol | Solvent | 30.00 |
| Disodium EDTA | Chelating Agent | 0.05 |
| Glycerin | Humectant | 1.0-5.0 |
| Triethanolamine | pH Adjuster | 0.15-1.0 |
| Ethylhexyl Palmitate | Solvent | 3.0-8.0 |
| Dimethicone | Skin Conditioning Agent | 1.0-5.0 |
| Octocrylene | Sunscreen Active | 4.0 |
| Oxybenzone | Sunscreen Active | 3.0 |
| Avobenzone | Sunscreen Active | 2.5 |
| Cetearyl Alcohol Dicetyl Phosphate Ceteth-10 Phosphate | Emulsifier | 2.0-4.0 |
| Acrylates/C12-22 Alkyl Methacrylate Copolymer | Film Former | 0.5-2.0 |
| Fragrance | Fragrance | 0.3 |

TABLE III

Thickeners Evaluation Using Rheology Measurements

| Ref# | Description | Viscosity (cP) @ shear rate = 1 | Flow point (Pa) | G"/G' | Sensory Characteristics |
|---|---|---|---|---|---|
| Sample 3 | Base formula A + 2% Hydroxypropyl Cellulose (Trade name - Klucel HCS) | 86890 | 117 | 0.414 | Slow rub-in, less cooling after immediately rub-in, and tacky skin feel |
| Sample 4 | Base formula A + 8% Cetearyl alcohol/Ceteareth-20/Glyceryl Monosearate/Stearic acid/Sodium acryloyl dimethyl taurate copolymer (Trade name - Jeesphere CPW SG2020L) | 76070 | 409 | 0.256 | Slow rub-in, less cooling after immediately rub-in, and bulk is thicker with some whitening |
| Sample 5 | Base formula A + 1% Sodium Acryloyldimethyltaurate/VP Crosspolymer (Trade name - Aristoflex AVS) | 49640 | 63 | 0.147 | Quick rub-in, more spreadable, cooling after immediately rub-in |
| Sample 6 | Base formula A + 1% Acrylic Acid/VP crosspolymer (Trade name - Ultrathix P-100) | 53880 | 69 | 0.114 | Quick rub-in and cooling after immediately rub-in |
| Sample 7 | Base formula A + 0.65% Sodium Acryloyldimethyltaurate/VP Crosspolymer (Trade name - Ultrez 21) | 74780 | 80 | 0.130 | Quick rub-in, cooling after immediately rub-in, but bulk is thicker with some whitening |

The compositions of the present disclosure may also comprise one or more additional ingredients selected from sunscreen active, skin conditioner, cooling enhancer, fragrance, and emollient. Including these ingredients in the present composition can change its rheology profile, and the amounts of thickener should be adjusted accordingly. The additional ingredients can be present in an amount of up to 30 percent, based on the total weight of the composition, or any subranges thereof.

The sunscreen active may be at least one UVA and/or UVB sunscreen comprising one or more hydrophilic organic screening agent, and/or one or more lipophilic organic screening agent, and/or one or more inorganic physical blocker. The physical blocking sunscreen active reflects or scatters ultraviolet radiation. Typical examples of physical blockers include titanium dioxide and zinc oxide.

Sunscreen actives according to the present disclosure can also be chemical absorbers that absorb harmful ultraviolet radiation. Chemical absorbers are classified, depending on the type of radiation they protect against, as either UVA or UVB absorbers. UVA absorber generally absorbs radiation in the 320 to 400 nm region of the ultraviolet spectrum, and UVB absorber generally absorbs radiation in the 280 to 320 nm region of the ultraviolet spectrum. Examples of sunscreen actives in the UV A and/or UVB range include anthranilate, benzophenone, dibenzoyl methane (avobenzone), p-aminobenzoic acid derivative, camphor derivative, cinnamate, salicylate, arnyldimethyl PABA, digalloyl trioleate, dioxybenzone, ethyl 4-bis(hydroxypropyl)aminobenzoate, 2-ethylhexyl-2-cyano-3,3-diphenylacrylate, glyceryl aminobenzoate, 3-imidazol-4-ylacrylic acid and ethyl ester, methyl anthranilate, octyldimethyl PABA, 2-phenylbenzimidazole-5-sulfonic acid and salt, sulisobenzone, N,N,N-trimethyl-4-(2-oxobom-3-ylidene methyl)anillinium methyl sulfate, and any combinations thereof. The sunscreen agent is present in an amount of 5 to 30 percent, based on the total weight of the composition, or any subranges therebetween. The sunscreen agent can also be present in an amount of 11.5 to 19 percent, based on the total weight of the composition, or any subranges therebetween The composition of the present disclosure may further comprise one or more skin conditioners selected from the group consisting of glycols (e.g., caprylyl glycol), silicones (e.g., dimethicone), aloe, vitamin C, derivatives of vitamin C, vitamin B, derivatives of vitamin B (e.g., panthenol) or a combination thereof. The skin conditioners may be present in an amount of from 1 to 8 percent, based on the total weight of the composition, or any subranges therebetween.

The composition of the present disclosure may further comprise one or more cooling enhancers consisting of menthol, menthol derivatives, menthyl lactate, menthyl PCA (pyrrolidone carboxylic acid), isopulegol, 3-(menthoxy)propane-1,2-diol, p-menthane-3,8-diol, vanillyl butyl ether, and ethyl methane carboxamide. The cooling enhancer is present in an amount of 0.01 to 1 percent, based on the total weight of the composition, or any subranges therebetween.

Table IV shows another base formula of the present disclosure, namely base formula B. Base formula B differs from base formula A in that the former includes some of the other ingredients discussed above, such as sunscreen active, conditioner, cooling enhancer, and fragrance. Table V shows how a stable viscous composition can be achieved by combining the thickener (the Aristoflex® previously identified in Table IV) with a gelling agent and emulsion stabilizer. The gelling agent used in Table V is a Gellan Gum (Kelcogel™ CG-HA) that is a polysaccharide produced by fermentation of a pure culture of *Sphingomonas elodea*. The emulsion stabilizer used in Table V is a Citrus Aurantium Sinensis (Orange) Fiber (Imulsi-Fi™ A30) that is an all-natural emulsion stabilizer made from orange pulp. Its distinctive cellular structure and unique protein and polysaccharide composition give this biopolymer an amphiphilic character (both hydrophilic and lipophilic properties), enabling it to lower the interfacial tension and stabilizing the oil/water interface very efficiently at ambient temperature.

It is shown in Table V that the rheology profiles of all these formulas are within the optimum range previously mentioned. It was also confirmed by an internal sensory panel, that Sample 8 and Sample 9 are spreadable, have fast rub-in, are not significantly whitening, and have cooling sensation.

TABLE IV

Base Formula B

| INCI NAME | FUNCTION/DESCRIPTION | wt. % Base Formula |
|---|---|---|
| DI Water | Solvent | QS. To 100 |
| Ethanol | Solvent | 30.00 |
| Disodium EDTA | Chelating Agent | 0.05 |
| Glycerin | Humectant | 1.0-5.0 |
| Triethanolamine | pH Adjuster | 0.15-1.0 |
| Ethylhexyl Palmitate | Solvent | 3.0-8.0 |
| Octocrylene | Sunscreen Active | 4.0-6.0 |
| Homosalate | Sunscreen Active | 5.0-10.0 |
| Avobenzone | Sunscreen Active | 2.5-3.0 |
| Cetearyl Alcohol | Emulsifier | 2.0-4.0 |
| Dicetyl Phosphate | | |
| Ceteth-10 Phosphate | | |
| Acrylates/C12-22 Alkyl Methacrylate Copolymer | Film Former | 0.5-2.0 |
| Silica | Opacifying Agent | 0.1-2.0 |
| Cooling enhancer | | 0.01-1.0 |
| Skin Conditioning Agent | | 1.0-8.0 |
| Fragrance | Fragrance | 0.35 |

TABLE V

Example of Obtaining Viscous Alcohol-Containing Composition Using Rheology Profile

| Ref# | Description | Viscosity (cP) @ shear rate = 1 | Flow point (Pa) | G"/G' | Sensory Result (HPT11-172) |
|---|---|---|---|---|---|
| Sample 8 | Base formula B + 1% Aristoflex AVS + 0.1% Gellen gum + 0.1% orange fiber | 55640 | 56 | 0.162 | More spreadable, less whitening, faster rub-in, and more cooling feel after immediately rub-in |
| Sample 9 | Base formula B + 1% Aristoflex AVS + 0.1% Gellen gum + 0.15% orange fiber | 48920 | 73 | 0.158 | More spreadable, less whitening, faster rub-in, and more cooling feel after immediately rub-in |
| Sample 10 | Base formula B + 1% Aristoflex AVS + 0.1% Gellen gum + 0.2% orange fiber | 51560 | 72 | 0.163 | Has the same spread ability and rub-in but has less whitening and more cooling feel after immediately rub-in |
| Sample 11 | Base formula B + 1% Aristoflex AVS + 0.1% Gellen gum + 0.25% orange fiber | 56920 | 91 | 0.155 | Has the same spread ability and rub-in but has more cooling feel after immediately rub-in |

Table VI shows another series of sample compositions for SPF 50 compositions. The rheology profiles of three compositions or formulas (Sample 12, Sample 13, and Sample 15) are within the optimum range. In comparing to current commercial products, the compositions of the present disclosure exhibit similar spreadability but have faster rub-in, less whitening, and more cooling sensation after immediately rubbing in. The rheology profile of Sample 14 is not within the optimum range. This formula became unstable over time. The reason for this is that it is SPF 60, meaning that it has a higher amount of sunscreen actives than Sample 12 and Sample 13, which are SPF 50. Sample 15 is also SPF 60, but it has slightly more gelling agent (0.15% as opposed to 0.1%). The additional amount of gelling agent accounts for the favorable viscosity characteristics in Sample 15.

TABLE VI

Example of Obtaining Viscous Alcohol-Containing Composition Using Rheology Profile

| Ref# | Description | Viscosity (cP) @ shear rate = 1 | Flow point (Pa) | G"/G' | Sensory Characteristics |
|---|---|---|---|---|---|
| Sample 12 | Base formula B + 1% Aristoflex AVS + 0.15% Gellen gum + 0.3% orange fiber | 55660 | 91 | 0.162 | Has the same spread ability but less whitening, faster rub-in and more cooling feel after immediately rub-in |
| Sample 13 | Base formula B + 1% Aristoflex AVS + 0.1% Gellen gum + 0.3% orange fiber | 53790 | 73 | 0.162 | Similar spread ability but less whitening, faster rub-in, and more cooling feel after immediately rub-in |
| Sample 14 | Base formula B + 1% Aristoflex AVS + 0.1% Gellen gum + 0.3% orange fiber | 27120 | 115 | 0.215 | more spreadable, less whitening, faster rub-in, and more cooling feel after immediately rub-in but not stable |
| Sample 15 | Base formula B + 1% Aristoflex AVS + 0.15% Gellen gum + 0.3% orange fiber | 41870 | 104 | 0.176 | Less spreadable but faster rub-in, less whitening, has more cooling feel after immediately rub-in |

While the present disclosure has been described with reference to one or more particular embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this disclosure.

What is claimed is:

1. A sunscreen composition, comprising:
   0.1 to 10 percent, based on the weight of the total composition, of a rheology modifying agent selected from the group consisting of a copolymer of acryloyldimethyltaurine and vinylpyrrolidone, a copolymer of acrylic acid and vinylpyrrolidone, acrylic-based anionic polymers, carbomers, and any combinations thereof;
   0.01 to 5 percent, based on the total weight of the composition, of a gelling agent selected from the group consisting of polysaccharides, polysaccharide gums, and a combination thereof; and
   10 to 40 percent, based on the total weight of the composition, of an aliphatic alcohol having 1 to 4 carbon atoms or a mixture thereof;
   5 to 30 percent, based on the total weight of the composition, of a sunscreen active; and
   0.01 to 5 percent, based on a total weight of the composition, of an emulsion stabilizer comprising natural fibers,
   wherein said composition provides a cooling sensation when rubbed on a user's skin.

2. The sunscreen composition of claim 1, wherein the natural fibers are from leaves, flowers, wood, fruits, or combinations thereof.

3. The sunscreen composition of claim 1, wherein said gelling agent is selected from the group consisting of starch, modified starch, cellulose, cellulose gum, pectin, gelatin, agar, alginate, gellan gum, and any combinations thereof.

4. The sunscreen composition of claim 1, wherein said alcohol is ethanol.

5. The sunscreen composition of claim 1, wherein said composition comprises 10 to 40 percent, based on the total weight of the composition, of said alcohol.

6. The sunscreen composition of claim 1, wherein said composition comprises 20 to 30 percent, based on the total weight of the composition, of said alcohol.

7. The sunscreen composition of claim 1, further comprising 1 to 8 percent, based on the total weight of the composition, of a skin conditioner.

8. The sunscreen composition of claim 7, wherein said skin conditioner is selected from the group consisting of glycols, silicones, aloe, vitamin C, derivatives of vitamin C, vitamin B, derivatives of vitamin B, and a combination thereof.

9. The sunscreen composition of claim 1, further comprising 0.01 to 1 percent, based on the total weight of the composition, of a cooling enhancer.

10. The sunscreen composition of claim 9, wherein said cooling enhancer is selected from the group consisting of menthol, menthol derivatives, menthyl lactate, menthyl PCA (pyrrolidone carboxylic acid), isopulegol, 3-(menthoxy)propane-1,2-diol, p-menthane-3,8-diol, vanillyl butyl ether, ethyl methane carboxamide, and any combinations thereof.

11. A sunscreen composition, comprising:
   0.1 to 10 percent, based on the weight of the total composition, of a rheology modifying agent selected from the group consisting of a copolymer of acryloyldimethyltaurine and vinylpyrrolidone, a copolymer of acrylic acid and vinylpyrrolidone, acrylic-based anionic polymers, carbomers, and any combinations thereof;
   0.01 to 5 percent, based on the total weight of the composition, of a gelling agent selected from the group consisting of starch, modified starch, cellulose, cellulose gum, pectin, gelatin, agar, alginate, gellan gum, and any combinations thereof;
   20 to 30 percent, based on the total weight of the composition, of an alcohol selected from the group consisting of aliphatic alcohols having one to four carbons;
   11 to 19.5 percent, based on the total weight of the composition, of a sunscreen active; and
   0.01 to 5 percent, based on the total weight of the composition, of an emulsion stabilizer comprising natural fibers, wherein said composition provides a cooling sensation when rubbed on a user's skin.

12. The sunscreen composition of claim 11, wherein the natural fruit fibers are from leaves, flowers, wood, fruits, or combinations thereof.

13. The sunscreen composition of claim 11, further comprising:
   1 to 8 percent, based on the total weight of the composition, of a skin conditioner selected from the group consisting of glycols, silicones, or a combination thereof; and
   0.01 to 1 percent, based on the total weight of the composition, of a cooling enhancer selected from the group consisting of menthol, menthol derivatives, menthyl lactate, menthyl pyrrolidone carboxylic acid, isopulegol, 3-(menthoxy)propane-1,2-diol, p-menthane-3,8-diol, vanillyl butyl ether, ethyl methane carboxamide, and any combinations thereof.

14. The sunscreen composition of claim 1, wherein the composition has a viscosity of from 10,000 to 90,000 centipoise.

15. The sunscreen composition of claim 1, wherein the composition has a viscosity of from 40,000 to 60,000 centipoise.

16. The sunscreen composition of claim 1, wherein the composition has:
   a ratio of a loss modulus to a storage modulus less than 0.19; or
   a flow point range from 20 Pa to 200 Pa.

17. The sunscreen composition of claim 1, wherein said sunscreen active is a physical blocking sunscreen active selected from the group consisting of titanium dioxide, zinc oxide, and a combination thereof.

18. The sunscreen composition of claim 1, wherein said sunscreen active is a chemical absorbing sunscreen.

19. The sunscreen composition of claim 18, wherein said chemical absorbing sunscreen is selected from the group consisting of anthranilate, benzophenone, dibenzoyl methane, p-aminobenzoic acid derivative, camphor derivative, cinnamate, salicylate, amyldimethyl PABA, digalloyl trioleate, dioxybenzone, ethyl 4-bis(hydroxypropyl)aminobenzoate, 2-ethylhexyl-2-cyano-3,3-diphenylacrylate, glyceryl aminobenzoate, 3-imidazol-4-ylacrylic acid and ethyl ester, methyl anthranilate, octyldimethyl PABA, 2-phenylbenzimidazole-5-sulfonic acid and salt, sulisobenzone, N,N,N-trimethyl-4-(2-oxobom-3-ylidene methyl)anillinium methyl sulfate, and any combinations thereof.

* * * * *